United States Patent
Stüwe (10) Patent No.: US 9,898,813 B2
(45) Date of Patent: Feb. 20, 2018

(54) METHOD FOR DETECTING FLAWS IN THE WALLS OF HOLLOW GLASS ITEMS

(71) Applicant: HEYE INTERNATIONAL GMBH, Obernkirchen (DE)

(72) Inventor: Hartwin Stüwe, Hespe (DE)

(73) Assignee: HEYE INTERNATIONAL GMBH, Obernkirchen (DE)

( * ) Notice: Subject to any disclaimer, the term of this patent is extended or adjusted under 35 U.S.C. 154(b) by 0 days.

(21) Appl. No.: 15/112,852

(22) PCT Filed: Oct. 20, 2014

(86) PCT No.: PCT/EP2014/002827
§ 371 (c)(1),
(2) Date: Jul. 20, 2016

(87) PCT Pub. No.: WO2015/127950
PCT Pub. Date: Sep. 3, 2015

(65) Prior Publication Data
US 2016/0379355 A1 Dec. 29, 2016

(30) Foreign Application Priority Data
Feb. 26, 2014 (DE) .................. 10 2014 002 582

(51) Int. Cl.
*G06T 7/00* (2017.01)
*G01N 21/90* (2006.01)

(52) U.S. Cl.
CPC .......... *G06T 7/0004* (2013.01); *G01N 21/90* (2013.01); *G06T 2207/30108* (2013.01)

(58) Field of Classification Search
CPC ........ G06T 7/0004; G06T 2207/30108; G01N 21/90
See application file for complete search history.

(56) References Cited

U.S. PATENT DOCUMENTS

| 5,204,911 A | 4/1993 | Schwartz et al. |
| 7,330,251 B2 | 2/2008 | Katayama et al. |
| 9,147,241 B2 | 9/2015 | Numazu |

FOREIGN PATENT DOCUMENTS

| CH | 652826 A5 | 11/1985 |
| EP | 0692710 B1 | 1/1996 |

(Continued)

OTHER PUBLICATIONS

PCT Notification of Transmittal of Translation of the International Preliminary Report on Patentability in International Application No. PCT/EP2014/002827, International Filing Date: Oct. 20, 2014. (dated Sep. 1, 2016).

(Continued)

*Primary Examiner* — Bhavesh Mehta
*Assistant Examiner* — Menatoallah Youssef
(74) *Attorney, Agent, or Firm* — Fox Rothschild LLP (57) ABSTRACT

The invention relates to a method for detecting defects in the walls of hollow glass items that rotate about their longitudinal axis during inspection, which method, in one form, is characterized by the production of an image series (4) that is binarised using a grey-scale value threshold image (5), wherein the threshold values of the threshold image (5) are measured differently according to the fixed positions of radiation-receiving elements used to display images. The images of the image series (10) formed by binarising the original image series (4) are combined in a histogram (6) that locally adds up the frequency of an occurrence of, inter alia, defect pixels representing static reflections within the sensor regions of the image series (10). Based on this histogram (6), a two-dimensional fade-out mask (12) is formed on which the regions of static reflections are combined, and by means of which the sensor regions (18) of the original image series (4) are masked, such that a masked image series (16) is produced, said series having images, in (Continued)

particular sensor regions characterized in that static reflections are faded out on same, whereby a subsequent flaw-detecting evaluation (17) of the images can be carried out, independent of their sequence.

18 Claims, 8 Drawing Sheets

(56) References Cited

FOREIGN PATENT DOCUMENTS

| EP | 1560018 A1 * | 8/2005 |
| WO | 8103706 A1 | 12/1981 |
| WO | 9641299 A1 | 12/1996 |
| WO | 2012172695 A1 | 2/2015 |

OTHER PUBLICATIONS

International Search Report in International Application No. PCT/EP2014/002827, International Publication No. WO 2015/127950, International Publication Date: Sep. 3, 2015, International Filing Date: Oct. 20, 2014. (dated Jan. 20, 2015).

* cited by examiner

METHOD FOR DETECTING FLAWS IN THE WALLS OF HOLLOW GLASS ITEMS

BACKGROUND

The invention relates to a method for detecting flaws and comparable, radiation-reflecting defects in the walls of hollow glass items.

Known from document CH 652826 A5 is a device for optically detecting flaws in transparent bodies, in which a number of radiation sources is allocated to a glass body that rotates around its longitudinal axis during an inspection. Located opposite the radiation sources are detectors accommodated in detector blocks as the radiation receivers. In order to counteract the reception of interference radiation, subsystems are formed that each consist of radiators and radiation receivers, wherein these subsystems are activated one after the other, and not simultaneously. These subsystems enable a suppression of interference radiation from the environment. However, a high level of experience is required for expediently creating the subsystems tailored to the individual case, here to the glass body to be inspected.

Interference radiation detracts from the strength of the evaluated received radiation, and can arise in a variety of ways from the ambient conditions, e.g., in the form of extraneous light sources, but can also stem from the shape of the hollow glass item to be inspected, e.g., reflections on rotationally symmetrical structural elements that are independent of a potential rotation of the hollow glass item, or the respective camera angle at which these reflections are recorded by a fixed radiation receiver. As a consequence, the received radiation is always composed of useful and interference signals.

A plurality of potential solutions has become known for separating useful and interference signals in conjunction with the flaw inspection of hollow glass items. EP 0 692 710 B1 describes a method and device for image processing to check for light-reflecting defects, wherein a hollow glass item rotates around its longitudinal axis, and wherein sequential images offset relative to each other by a rotational angle are generated by an incident light beam as a function of rotation. By comparing at least two sequential images, constantly reflected scatter reflections are differentiated from variable useful reflections pointing to local defects of the hollow glass item during the evaluation. As a consequence, the evaluation of reflections here depends on the sequence of the first images.

The differentiation between useful and interference signals is of significant importance during the automated flaw detection in hollow glass items. A faulty interpretation of an interference signal as a useful signal results in an item being discarded unnecessarily as unusable. As a consequence, there exists a strong interest in effectively detecting and masking out any interference signals, so that the respective item can be inspected based exclusively on useful signals.

SUMMARY OF THE INVENTION

The object of the invention is to improve a method of the kind described at the outset with an eye toward reliably masking out or suppressing interference signals and achieving a simpler implementability. This object is achieved by the present invention which, in one form, provides a method for detecting flaws and comparable, radiation-reflecting defects in the walls of hollow glass items. Static radiation emitted by radiation elements, reflected on the hollow glass item, and containing interference reflections and dynamic, defect-indicating reflections, are received by several spaced apart, radiation receiving elements fixed in place relative to the hollow glass item rotating around its longitudinal axis. The radiation received forms an original image series consisting of several images recorded based on various recording angles. A binarized image series containing static and dynamic reflections is produced from the original image series. The dynamic reflections are removed from the image series and a fade-out mask that only images static reflections is generated. The image series is masked with the fade-out mask so as to mask out the regions of static reflections and produce a masked image series of the hollow glass item. The images of the image series are used to detect the defects.

It is essential to the invention that an original image series also containing defect features be generated from the hollow glass item rotating around its longitudinal axis to be inspected for the presence of defects, wherein it consists of individual images on which sensor regions are imaged that show parts of the hollow glass item at different viewing angles. This original image series is used to produce a binarized image series, which serves to acquire cumulatively arising reflections, wherein a two-dimensional image is generated based upon this binarized image series, and used to manufacture a fade-out mask. Also essential is that the fade-out mask fabricated in this way be used to mask the image series mentioned at the outset, which images the hollow glass item, consists of sensor regions, and also contains static reflections, thereby giving rise to a masked image series, which no longer contains any static reflections, and is taken as the basis for continued evaluation only as regards the presence of defects in the form of dynamic reflections.

According to additional features, the fade-out mask is generated by means of a histogram based on adding together the frequency values of the pixels of all images of the binarized image series that describe respective significant reflections, wherein this histogram is further used to manufacture the fade-out mask. The chronological sequence of the images in the image series to be evaluated is unimportant to the process of adding together the frequency values. The fade-out mask consists of a two-dimensional compilation in the sensor regions of the histograms in which the pixel regions that can be interpreted as static reflections are referred to as "clouds" in each of the sensor regions. In order to distinguish between static and dynamic reflections within the framework of generating the binarized image series, it is possible to draw upon the circumstance that the static reflections, contrary to the dynamic reflections, are uniformly present in many images of the original image series, regardless of the viewing or rotational angle of the hollow glass item, so that all techniques familiar to the expert that are based upon this circumstance can be used to separate static and dynamic reflections within the framework of the invention.

According to other features, the fade-out mask is used to mask a compressed image series that exhibits static and dynamic reflections. This is the original image series that represents the hollow glass item or parts thereof at different viewing angles while turning the latter. By using a compressed image series proceeding from this originally recorded image series, the evaluation can be confined to portions of the images of the hollow glass item acquired by the sensor regions that are deemed as especially relevant. The user can individually determine which portions are here involved.

In this conjunction, the term "sensor region" describes the portion of the hollow glass item to be inspected that was acquired and imaged by a respective radiation receiving element or sensor.

The features of other embodiments are geared toward the configuration of the procedural step, whose objective is to obtain the fade-out mask from the added together frequency values of the histogram image. To this end, a morphological operation along with a binarization is performed based on a threshold value (number of images–x), wherein the number of images is here the number of images in the original series, and wherein "x" is a user selectable value equal to a positive whole number, for example 1 to 20, so that the threshold value defined in this way describes the percentage of original images that satisfies the condition that a frequency value lying above will arise and be considered during the evaluation. A user selectable tolerance range is defined for the frequency value in this way, which only when exceeded prompts any consideration.

Other features are geared toward a configuration of the binarization method of the original image series, which is aimed at generating the binarized series mentioned above. By individually determining the threshold values for binarizing the individual sensor regions, among other things as a function of the position of the radiation receiving elements, in conjunction with adding together the frequency values of pixels that describe dominant reflections, a distinction is made between static and dynamic reflections. This results in a histogram image that visualizes the position and frequency distribution of the individual pixels, to the extent that their respective frequency value lies above the threshold value of the individual sensor region. Only under this condition will a region characterized by this pixel be interpreted as a region in which static reflections were detected.

Further features are geared toward further processing the added together frequency of the histogram representing the pixels that can be interpreted as a static reflection. It is essential that, due to the tolerance regions of the pixel positions, the image derived from the histogram image can exhibit gaps between the individual positions, which are processed with image processing methods for generating a further two-dimensional image that can be used as a fade-out mask. This results in "cloudy" surface regions of each sensor region, which are interpreted as regions of static reflections.

According to still other features, the histogram image is further processed to obtain the fade-out mask in a morphological operation and/or a threshold value binarization. Also, the images of the masked image series can be evaluated in any sequence desired within the framework of defect detection. By comparison to prior art, this circumstance provides latitude in the specific configuration of the further evaluation method.

Other features are geared toward the further configuration of the image series, images and sensor regions to be recorded within the framework of implementing the method, including their parameters. These include features wherein the original, binarized and/or masked image series include a number of images that is determined by the number of rotations of the hollow glass item around its longitudinal axis, and represents the hollow glass item or regions thereof at different rotational angles. These also include features wherein each image of the original, binarized and/or masked image series consists of a number of sensor regions corresponding to the number of radiation receiving elements As evident, the method according to the invention introduces an automated, reproducible method for preparing image series to be used in determining defects, based upon which the result of a defect detection can be improved so as to prevent misinterpretations of reflections.

BRIEF DESCRIPTION OF THE DRAWINGS

The invention will be explained in greater detail below drawing reference to the attached figures. Shown on.

DETAILED DESCRIPTION OF THE INVENTION

The hollow glass item 1 to be inspected for the presence of defects, such as flaws, is made to rotate around its longitudinal axis 2 for executing the inspection, wherein a plurality of radiation receiving elements, in the present case twenty sensors fixed in place spaced apart from each other, is used to record eighty images 3 one after the other during the rotation based on their fixed angular positions. To this end, the sensors are each connected with a high-speed camera (not graphically depicted) via image conductors. These images 3 form an original image series 4 of the hollow glass item 1, which is taken as the basis for the subsequent evaluation.

Each of the images 3 consists of a number of sensor regions 18 corresponding to the number of sensors. As indicated above, each sensor region 18 describes the portion of the hollow glass item to be inspected that was acquired and imaged by a respective radiation receiving element or sensor. To this end, the hollow glass item 1 is radiated with radiation elements (also not graphically depicted), wherein static interference reflections or signal components caused by specific rotationally symmetrical features of the hollow glass item 1, e.g., signal components caused by a bottleneck thread, which are irrelevant to an evaluation and must therefore be removed, get into the receiving area of the sensors in addition to dynamic reflections, for example which indicate a flaw. The images 3 of the image series 4 present as grayscale images thus contain both signal components.

Figure 5:
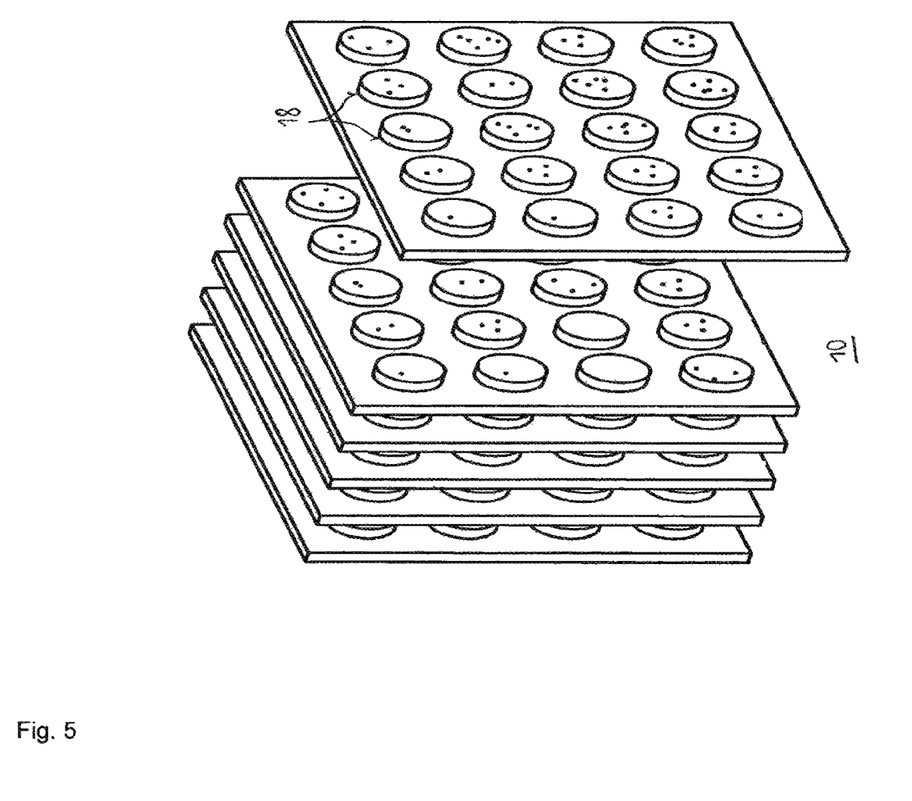
FIG. 5 is a view of the image series after binarization (with threshold values added)

Flaws appear on the images 3 as bright white spots, the position of which on the images or their sensor regions 18 (FIG. 5) change based on the rotational angle of the hollow glass item 1 around the axis 2, while the interference reflections caused by the rotationally symmetrical structural features only minimally change their position on the images 3 during the rotation, or not at all. This circumstance is used in a manner to be described below for separating the so-called signal components.

Figure 1:
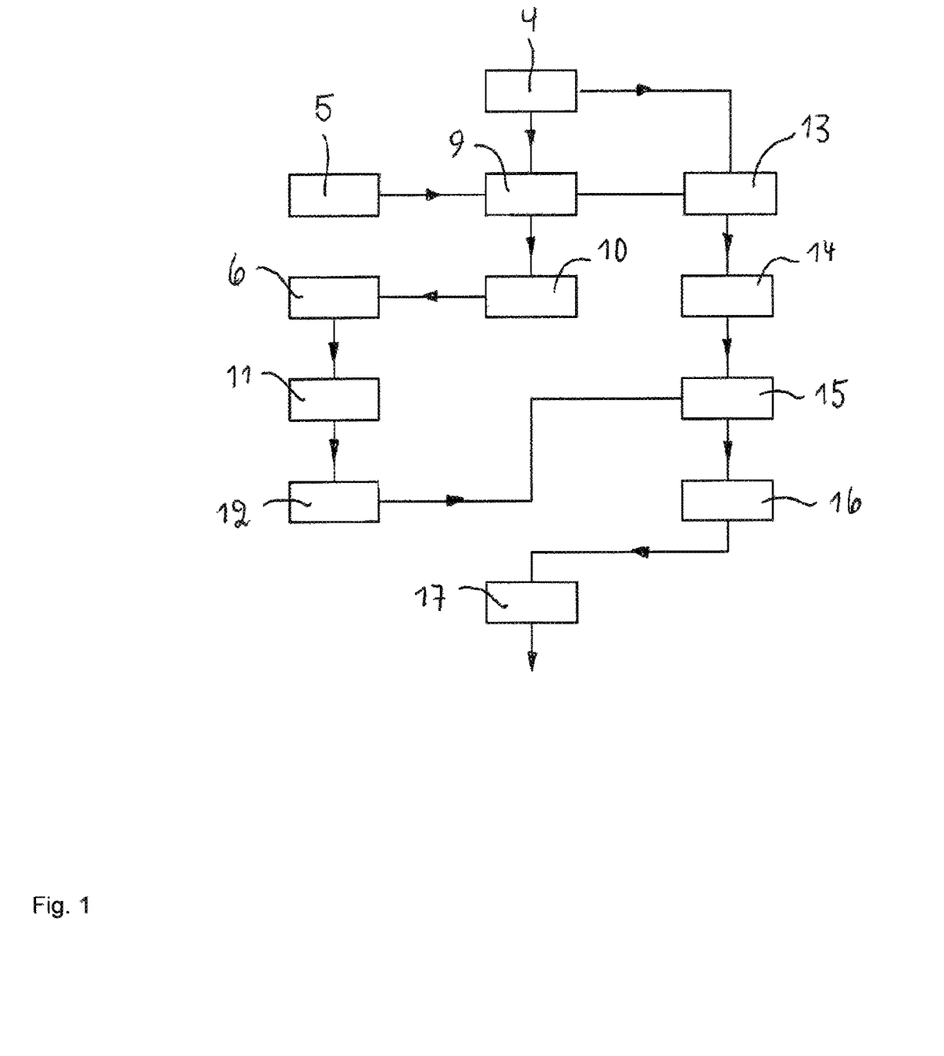
FIG. 1 is a schematic view of the procedural sequence according to the invention.
Figure 2:
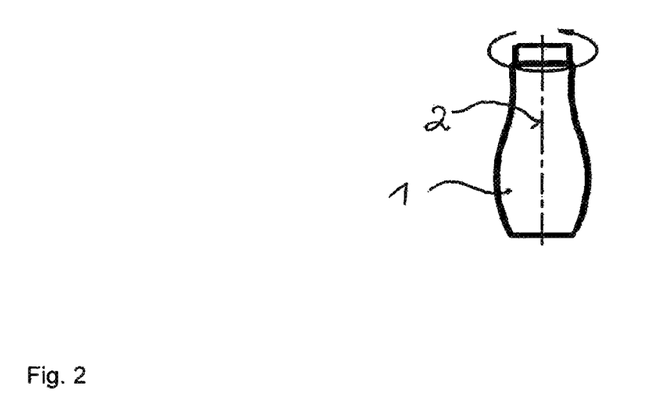
FIG. 2 is a rotating hollow glass item for recording an image series.
Figure 3:
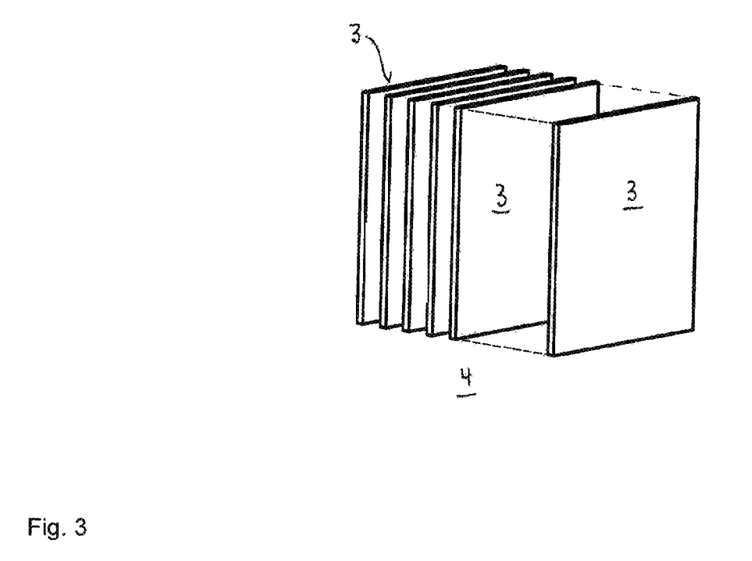
FIG. 3 is a view of an image series recorded by a hollow glass item.
Figure 4:
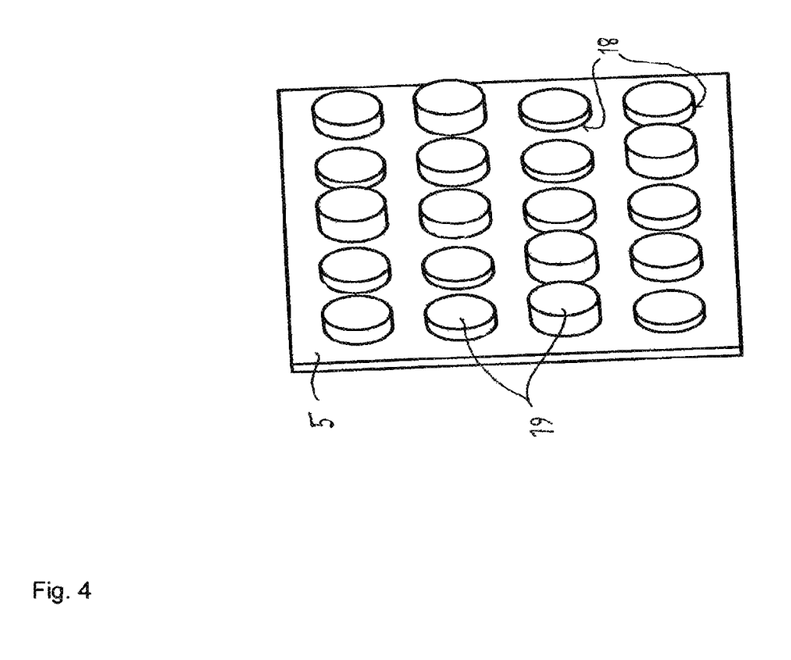
FIG. 4 is a view of the threshold values for binarizing sensor regions.

Marked 5 (FIG. 4) is a grayscale threshold image, on which various threshold values 19 are allocated to the various sensor regions 18 of the mentioned twenty sensors as a function of their respective position relative to the rotating hollow glass item 1. The threshold values 19 are superposed with the gray values of the sensor regions 18 of the images 3. This yields a binarized image from each of the original grayscale images of the image series 4, which contains the position of dynamic and static reflections. Each pixel of a sensor region 18 whose gray value lies above its respective threshold value 19 is interpreted as a spot pixel, and each pixel whose gray value lies under the respective threshold value 19 is interpreted as a background. As a consequence, each piece of information in the sensor region 18 obtained within the framework of this binarization 9 contains components that describe spot pixels, and components that describe background pixels. The original image series 4 gives rise to a binarized image series 10, whose sensor regions 18 image static and dynamic signal components.

Figure 6:
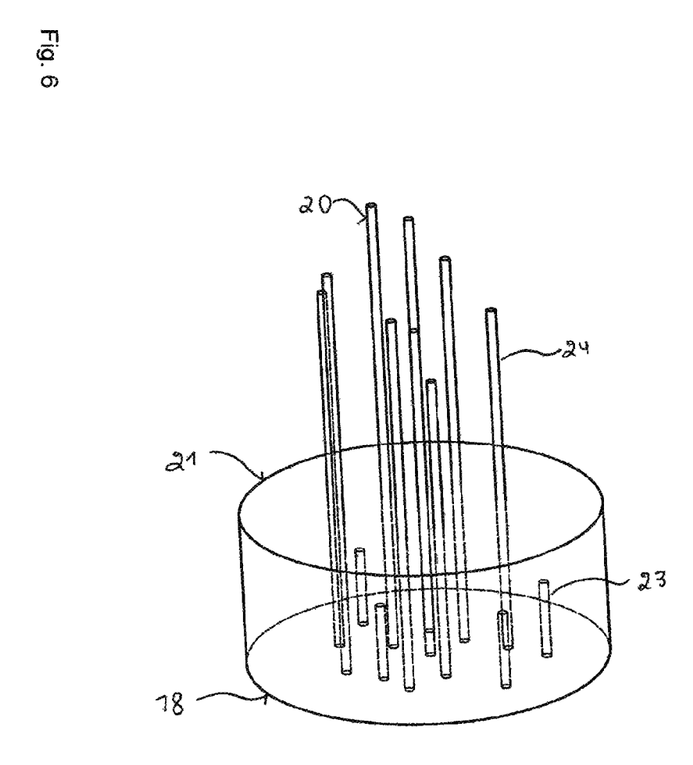
FIG. 6 is a view of a histogram for a sensor region.

A summary of results from the binarized image series 10 is generated in an image in a histogram image 6 (FIG. 7) by depicting the frequency with which a spot pixel arises locally, i.e., relative to the pixel position of each sensor region 18. As an evaluation of the binarized image series 10, the histogram image 6 contains twenty sensor regions 18, within which the respective positions of the spot pixels are visible. For the sake of simplicity, FIG. 7 does not show the variability of the individual threshold values 21 of the sensor regions 18. However, a pixel of a sensor region 18 is only interpreted as a relevant spot pixel based upon its cumulative frequency 20 if the frequency value lies above the respective threshold value 21 of the sensor region 18. (FIG. 6) As evident, the pixels allocated to the individual sensor regions 18 encompass those which describe dynamic signal components 23, whose value lies under the respective threshold value 21, and those signal components 24 whose value lies above the threshold value 21.

The histogram image 6 is binarized using a threshold value corresponding to the value (number of images–x), wherein the value "x" can be selected by the user, and can be selected for each sensor region 18. In the present case, the threshold value thus corresponds to a value of (80–x). Each region above this threshold 21 describes the position of a static spot pixel, and appears as a single point 11 in an image 7, which also exhibits gaps in the spot pixel regions. As a consequence, the value "x" can be used to determine the threshold 21 at a given number of images. This value "x" can be individually defined for each sensor region.

The image 7 is characterized by a number of sensor regions 18, whose number in turn corresponds to that of the radiation receiving elements mentioned at the outset. Proceeding from this image 7, an image 8 usable as a two-dimensional fade-out mask 12 and again comprised of sensor regions 18 is fabricated in a morphological operation 25 geared toward closing these gaps. In the framework of this operation, the determined spot pixels are thus enhanced by the tolerance-related range of variation, and the existing gaps are closed in this way. This gives rise to cloudlike regions 22 that describe the position of spot pixels.

Figure 7:
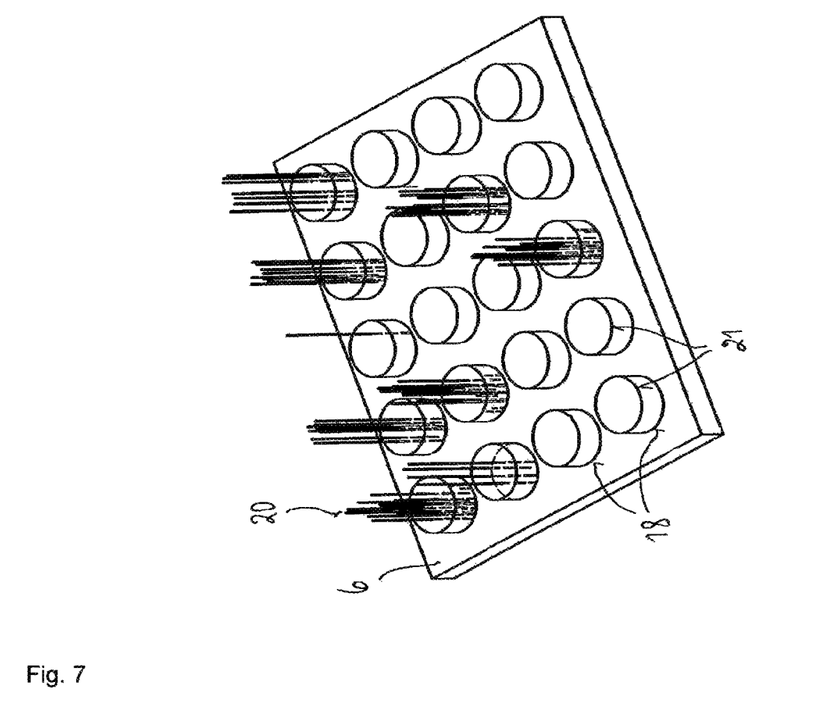
FIG. 7 is a view of a histogram image with varying threshold values for each sensor region.
Figure 8:
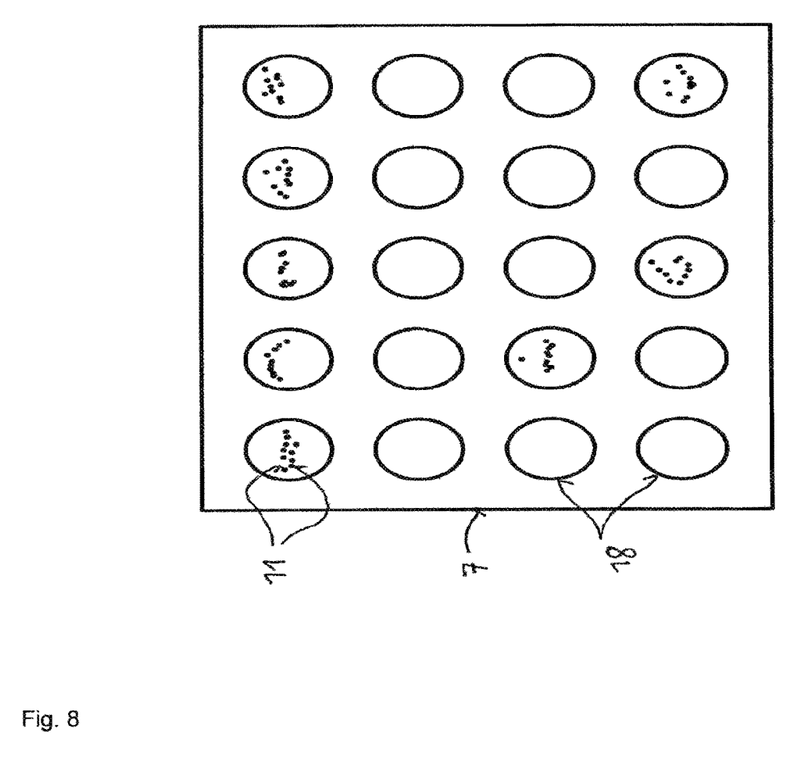
FIG. 8 is a view of a fade-out mask image with gaps.
Figure 9:
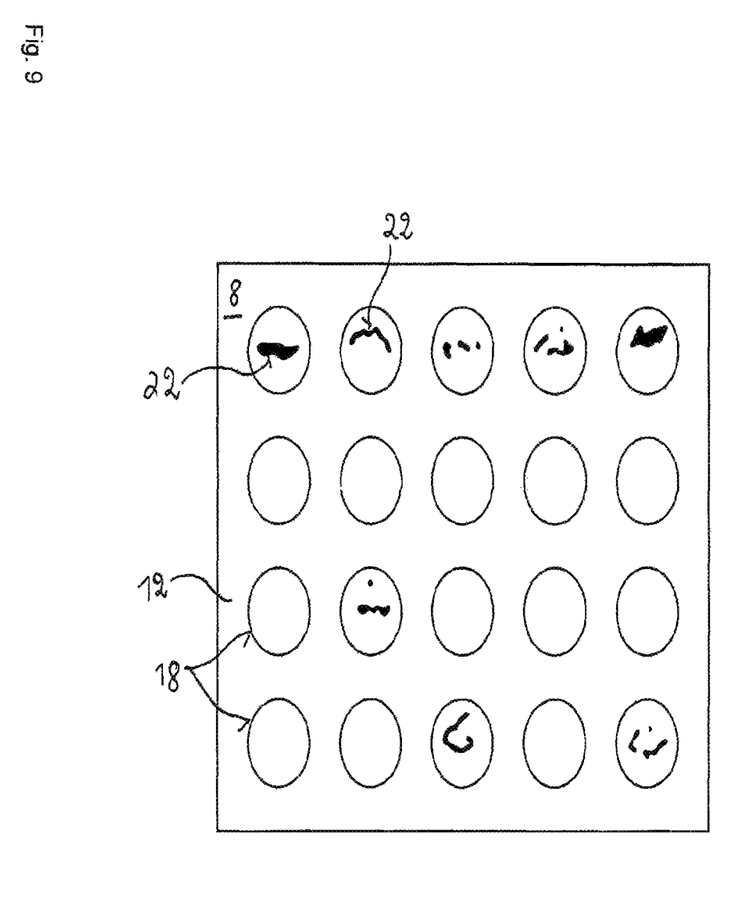
FIG. 9 is a view of a fade-out mask.

The histogram 6 along with FIGS. 7 and 8 each exhibit a surface that corresponds to a camera image of the high-speed camera mentioned at the outset.

The image series 4, whose images 3 in the sensor regions 18 are present as a grayscale distribution in the initial state, is subjected to an image background separation 13 proceeding from the evaluation zones determined by the user (area of interest, AOI). This measure serves to remove those image components from the mapped sensor regions 18 that are irrelevant to a continued evaluation, eliminating the need for any closer examination. The result is an image series 14 that now just contains the zones in the sensor regions 18 earmarked by the user for evaluation. These zones describe the position of both static and dynamic reflections. The images of the image series 14 generated in this way each exhibit a surface corresponding to a camera image of the high-speed camera. Each point, and hence the location of each individual pixel, can be localized on these images by means of a coordinate system.

The images of the image series 14 are subsequently marked with the fade-out mask 12, so that this masking 15 results in a masked object image series 16, on whose individual images the spot pixel regions that describe static reflections are faded out. This yields a series of images with masked zones in the sensor regions 18, which are prepared for an evaluation 17 to determine the occurrence of flaws and comparable defects. The image regions of the interference reflections are already eliminated by the masking with the fade-out mask.

REFERENCE LIST

1. Hollow glass item
2. Longitudinal axis
3. Image
4. Image series
5. Threshold image
6. Histogram image
7. Image
8. Image
9. Binarization
10. Binarized image series
11. Point
12. Fade-out mask
13. Image background separation
14. Compressed image series
15. Masking
16. Masked image series
17. Evaluation
18. Sensor region
19. Threshold value for spot pixel determination
20. Frequency
21. Threshold value
22. Region
23. Signal component
24. Signal component
25. Operation

What is claimed is:

1. A method for detecting flaws and comparable, radiation-reflecting defects in the walls of a hollow glass item, comprising;
    (a) reflecting static radiation, emitted by radiation elements, from the hollow glass item rotating around its longitudinal axis, said reflected radiation and containing interference reflections and dynamic, defect-indicating reflections;
    (b) receiving said reflected radiation by several spaced apart, radiation receiving elements fixed in place relative to the hollow glass item;
    (c) forming from said received radiation an original image series consisting of several images recorded based on various recording angles, wherein each of the images of the original image series comprise sensor regions;
    (d) producing from the original image series a binarized image series containing static and dynamic reflections;
    (e) removing from the binarized image series the dynamic reflections and generating a fade-out mask that only images static reflections;

(f) masking the original image series with the fade-out mask so as to mask out the regions of static reflections and produce a masked image series of the hollow glass item;

(g) detecting the defects using the images of the masked image series; and wherein a compressed image series containing both static and dynamic reflections is generated proceeding from the original image series, and that the compressed image series is used to generate the masked image series by means of the fade-out mask.

2. The method according to claim 1,
wherein the binarized image series is processed to generate a two-dimensional histogram image that displays cumulative frequency values of the static and dynamic components of all images of the original image series, and that the histogram image is further processed to generate the fade-out mask containing only static reflections.

3. The method according to claim 2,
wherein the histogram image is further processed to generate the fade-out mask via binarization based on a threshold value (number of images−x).

4. The method according to claim 3,
wherein x is a positive, whole number with x>1.

5. The method according to claim 2,
wherein the sensor regions include information regarding pixels, and wherein the sensor regions and the position of the pixels are compiled in the histogram image.

6. The method according to claim 1,
wherein several of said sensor regions are combined in each image of the original image series.

7. The method according to claim 1,
wherein the original image series is binarized by means of a grayscale threshold image, wherein the sensor regions of each image of the original image series have allocated to them various threshold values, which depend among other things on the position of the radiation receiving elements.

8. The method according to claim 2,
wherein:
the original image series is binarized by means of a grayscale threshold image, the sensor regions of each image of the original image series have allocated to them various threshold values, which depend among other things on the position of the radiation receiving elements, and a two-dimensional image that can be used as a fade-out mask is produced out of the histogram image through binarization and possible further processing.

9. The method according to claim 2,
wherein: the original image series is binarized by means of a grayscale threshold image, the sensor regions of each image of the original image series have allocated to them various threshold values, which depend among other things on the position of the radiation receiving elements, and the histogram image is further processed to obtain the fade-out mask in at least one of a morphological operation and a threshold value binarization.

10. The method according to claim 1, characterized in that wherein the images of the masked image series are individually evaluated in whatever sequence desired in order to detect defects.

11. The method according to claim 1,
wherein the original, binarized and masked image series include consist of a number of images that is determined by the number of rotations of the hollow glass item around its longitudinal axis, and represents the hollow glass item or regions thereof at different rotational angles.

12. The method according to claim 1,
wherein each image of the original, binarized and masked image series consists of a number of sensor regions corresponding to the number of radiation receiving elements.

13. The method according to claim 1, wherein the histogram image is further processed to generate the fade-out mask via binarization based on a threshold value (number of images−x).

14. The method according to claim 13,
wherein x is a positive, whole number with x>1.

15. The method according to claim 4,
wherein the sensor regions include information regarding pixels, and wherein the sensor regions and the position of the pixels are compiled in the histogram image.

16. The method according to claim 2,
wherein several of said sensor regions are combined in each image of the original image series.

17. The method according to claim 2,
wherein the original image series is binarized by means of a grayscale threshold image, wherein the sensor regions of each image of the original image series have allocated to them various threshold values, which depend among other things on the position of the radiation receiving elements.

18. The method according to claim 2,
wherein the images of the masked image series are individually evaluated whatever sequence desired to detect defects.

* * * * *